US010392645B2

(12) United States Patent
Petersen et al.

(10) Patent No.: US 10,392,645 B2
(45) Date of Patent: Aug. 27, 2019

(54) PROTEIN HYDROLYSATE AND METHOD FOR MAKING A PROTEIN HYDROLYSATE

(71) Applicants: Brent L. Petersen, Twin Falls, ID (US); Niels J. Palmer, Twin Falls, ID (US); Byron M. Toledo, Twin Falls, ID (US); Jerry O'Dea, Fitchburg, WI (US); Loren S. Ward, Twin Falls, ID (US)

(72) Inventors: Brent L. Petersen, Twin Falls, ID (US); Niels J. Palmer, Twin Falls, ID (US); Byron M. Toledo, Twin Falls, ID (US); Jerry O'Dea, Fitchburg, WI (US); Loren S. Ward, Twin Falls, ID (US)

(73) Assignee: GLANBIA NUTRITIONALS(IRELAND) LTD., Kilkenny (IE)

(*) Notice: Subject to any disclaimer, the term of this patent is extended or adjusted under 35 U.S.C. 154(b) by 148 days.

(21) Appl. No.: 15/184,990

(22) Filed: Jun. 16, 2016

(65) Prior Publication Data

US 2016/0369317 A1 Dec. 22, 2016

Related U.S. Application Data

(60) Provisional application No. 62/180,129, filed on Jun. 16, 2015.

(51) Int. Cl.
*C12P 21/06* (2006.01)
*A23J 3/34* (2006.01)
*A23L 33/18* (2016.01)

(52) U.S. Cl.
CPC .............. *C12P 21/06* (2013.01); *A23J 3/343* (2013.01); *A23L 33/18* (2016.08); *C12Y 304/14002* (2013.01)

(58) Field of Classification Search
CPC ...................................................... C12P 21/06
See application file for complete search history.

(56) References Cited

U.S. PATENT DOCUMENTS

| 8,101,377 B2 * | 1/2012 | Blanton | A23G 1/44 435/41 |
| 2006/0134310 A1 * | 6/2006 | Cho | A23J 1/148 426/656 |
| 2013/0344200 A1 * | 12/2013 | Yin | A23B 4/03 426/63 |

* cited by examiner

*Primary Examiner* — Rosanne Kosson
(74) *Attorney, Agent, or Firm* — Donna J. Russell

(57) ABSTRACT

Disclosed is a simplified method for producing a protein hydrolysate, the method having the advantages of decreasing costs associated with energy, materials, and space as compared to that of conventional methods. A protein hydrolysate/enzyme composition is also disclosed.

12 Claims, 1 Drawing Sheet

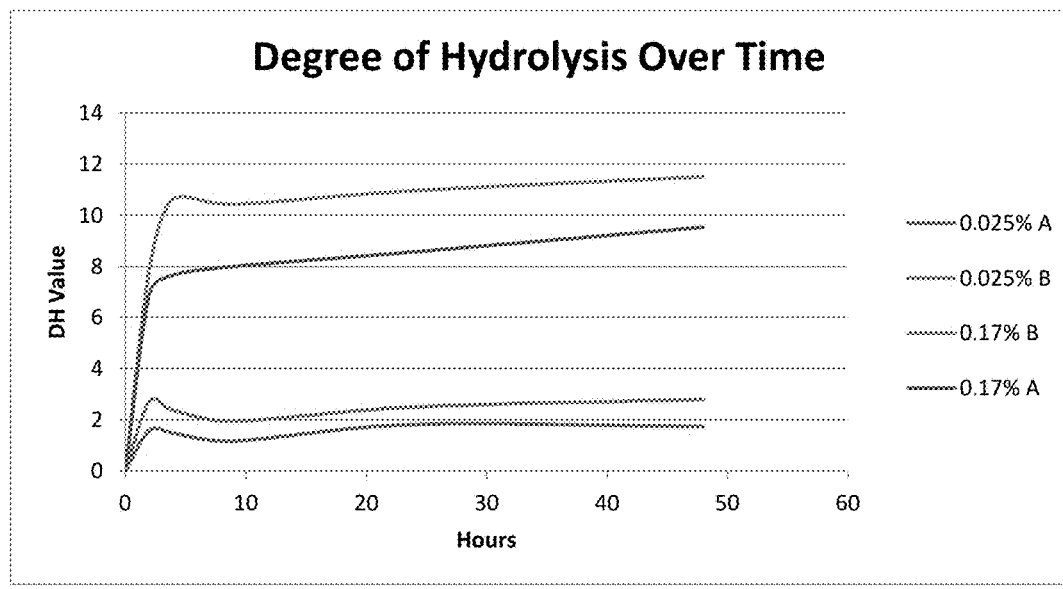

PROTEIN HYDROLYSATE AND METHOD FOR MAKING A PROTEIN HYDROLYSATE

FIELD OF THE INVENTION

The invention relates to methods for hydrolyzing proteins. More specifically, aspects of the invention relate to methods for producing hydrolyzed whey proteins.

BACKGROUND OF THE INVENTION

There are two general categories of commonly used methods for protein hydrolysis: enzymatic and chemical (e.g., acid or alkali). Chemical hydrolysis can be more difficult to control and may have the potential to reduce the nutritional quality of the resulting hydrolysates. Enzymes, on the other hand, generally hydrolyze proteins under milder conditions of temperature and pH than those which are used in alkaline or acid hydrolysis, and can target specific peptide bonds. Protein hydrolysis in the food industry generally involves the use of digestive proteolytic enzymes from animals (e.g. trypsin, pepsin, chymotrypsin) and/or food-grade enzymes from plants or microorganisms (e.g., bacteria, fungi).

A protein hydrolysate is a complex mixture of peptides of different chain lengths, together with free amino acids, the fraction of peptide bonds that have been cleaved in the starter protein being known as degree of hydrolysis (DH). Protein hydrolysis can be complicated by undesired molecular interactions, such as formation of insoluble protein aggregates, or gels.

Milk proteins, and especially whey proteins, provide a significant source of biologically active peptides. Peptides having antithrombotic, antihypertensive, analgesic, and other effects have been described, and are often inactive within the parent protein and activated when released by enzymatic hydrolysis.

Trends in food production which are intended to provide protein in more bioavailable forms, include providing proteins as hydrolysates because it makes more of the biologically active peptides readily available when consumed in a protein supplement, food, beverage, etc. Another option that recently has become popular is supplementation of the normal digestive enzymes with enzyme supplements, such as those from *Aspergillus* species, as well as incorporating those enzyme supplements into whey protein products so that they can presumably aid in protein digestion once the protein has been consumed.

Conventional methods for enzymatic hydrolysis of proteins generally involve series of steps, generally including steps such as diluting the protein with water, heating to achieve an optimum temperature range for the enzyme(s) used, pH adjustment, an additional heating step for the purpose of deactivating the enzyme(s), and one or more steps for increasing the solids content of the hydrolysate before it is dried. For example, U.S. Pat. No. 4,482,574 (C. Lee, 13 Nov. 1984) discloses a method having the steps of "(a) adjusting the pH of an aqueous solution of a proteinaceous material in which at least 50% of the protein is soluble in water at an alkaline pH ranging from about 7 to about 10 to a pH within the range of from about 7.5 to about 10 and at least 0.5 pH units above the native pH of the solution of proteinaceous material, said solution having a temperature of less than about 30° C., the total dissolved protein content ranging from about 0.5% and about 20% by weight when determined at said pH; (b) heating the alkaline solution of step (a) to an elevated temperature within the range of from about 50° C. and about 150° C. at a rate insufficient to cause gelation of the solution; (c) cooling said heated solution to a temperature within the range of from about 30° C. to about 2° C. within 1 hour after the said solution reaches its maximum temperature level, said cooling being conducted at a rate sufficient to prevent gelation of said protein containing solution; and (d) enzymatically hydrolyzing the protein in the so treated solution to convert the protein to a hydrolyzate."

U.S. Pat. No. 8,101,377 (M. V. Blanton et al., 24 Jan. 2012) discloses a method having the steps of "providing a solution comprising at least one dairy protein; adjusting the pH of the solution to about 10.4 or more to form a basic protein solution, cooling the basic protein solution by adjusting the temperature of the solution to about 50° F. or less; and adding a protease enzyme to the basic, cooled protein solution, wherein the protease enzyme converts at least a portion of the dairy protein to dairy protein hydrolysates having a weight average molecular weight of about 1000 to about 10,000 Daltons."

Guo et al. (Guo, Y. et al., Optimisation of hydrolysis conditions for the production of the angiotensin-I converting enzyme (ACE) inhibitory peptides from whey protein using response surface methodology, *Food Chemistry* (2009) 114: 328-333) utilized a method that involved heating the protein at 65 degrees Celsius (149 degrees Fahrenheit), cooling the protein solution to the hydrolysis temperature, and adjusting the pH with 0.1 N NaOH. The pH was maintained during hydrolysis by the continuous addition of 0.1 N NaOH, and the reaction was stopped by heating the solution for 20 minutes at 80 degrees Celsius (176 degrees Fahrenheit) to deactivate the enzyme.

What are needed are new and better ways, which preferably will require fewer steps, decrease the need for the addition of compounds used for pH adjustment, and decrease added chemical, energy, and other costs, to produce protein hydrolysates. In product fields such as nutritional supplements and performance nutrition products, for example, it would also be advantageous to combine the beneficial effects of protein hydrolysates and proteolytic enzymes to further improve the bioavailability of bioactive peptides from proteins, and especially from whey proteins, which have been shown to be a significant source of such bioactive peptides.

SUMMARY OF THE INVENTION

The invention relates to a method for producing a hydrolyzed protein product, the method comprising the steps of admixing at least one proteolytic enzyme with at least one protein to produce a protein/enzyme admixture and holding the protein/enzyme admixture for a period of time under agitation to produce a hydrolyzed protein/enzyme admixture, the method being performed without the steps comprising/consisting of heating the protein, the at least one proteolytic enzyme, the protein/enzyme admixture, or a combination thereof, to increase the activity of the at least one proteolytic enzyme in the admixture; adjusting the pH to optimize the activity of the at least one proteolytic enzyme; and heating the protein/enzyme admixture to inactivate the at least one proteolytic enzyme. The method may, however, further comprise at least one step of drying the hydrolyzed protein/enzyme admixture (i.e., co-drying the protein(s) and enzyme(s)), such as, for example, by spray-drying. In various aspects, the protein can be whey protein. In various aspects, the whey protein is selected from the group consisting of whey protein isolate, whey protein concentrate, and combinations thereof.

The period of time during which the protein/enzyme admixture is held is, in various aspects of the invention, about 1 to about 72 hours, about 4 to about 8 hours, from about 6 to about 8 hours, from about 6 to about 24 hours, from about 6 to about 72 hours, etc., the time being determined by one of skill in the art according to the degree of hydrolysis desired in the hydrolysate produced thereby. In various aspects of the invention, the protein/enzyme admixture is held at a temperature of from about 33 to about 50 degrees Fahrenheit, which includes subranges thereof, such as 33 to 45 degrees Fahrenheit, for example.

The invention also relates to at least one product produced by the method. Some aspects of the invention relate to a composition comprising a co-dried hydrolyzed protein/enzyme product produced by a method comprising the steps of admixing at least one proteolytic enzyme with at least one protein to produce a protein/enzyme admixture, holding the protein/enzyme admixture under agitation for a period of time sufficient to produce a protein hydrolysate/enzyme admixture, the method being performed without additional steps selected from the group of steps consisting of heating the protein, at least one proteolytic enzyme, protein/enzyme admixture, or a combination thereof, to increase the activity of the enzyme in the protein/enzyme admixture; adjusting the pH to optimize the activity of the at least one proteolytic enzyme; heating the hydrolyzed protein/enzyme admixture to inactivate the at least one proteolytic enzyme; and combinations thereof. The method may further comprise the step of drying the hydrolyzed protein/enzyme admixture, such as, for example, by spray-drying.

Enzymes may be selected from the group consisting of proteolytic enzymes (i.e., proteases) of plant, animal, fungal, algal, or bacterial origin, as well as combinations thereof.

BRIEF DESCRIPTION OF THE DRAWINGS

FIG. 1 is a graph illustrating the results of analysis of levels of hydrolysis performed on two separate days (A and B). Samples were taken at time points from 0 to 48 hours, and the degree of hydrolysis was measured for each sample. The experiment was run using enzyme at 0.025% and 0.17% on each day.

DETAILED DESCRIPTION

The inventors have developed a method for hydrolyzing protein and producing hydrolyzed protein compositions, the advantages of the method including, for example, reducing energy costs for hydrolysate production, reducing space requirements for hydrolysate production, and reducing water and other materials costs associated with hydrolysate production, as compared to those costs associated with hydrolysate production accomplished by conventional methods currently known to those of skill in the art. The method comprises admixing at least one proteolytic enzyme with at least one protein to produce a protein/enzyme admixture and holding the protein/enzyme admixture under agitation for a period of time sufficient to produce a protein hydrolysate/enzyme admixture having a desired degree of protein hydrolysis; wherein the method is performed without the steps of heating and/or adjusting the pH to optimize the activity of, or to deactivate, the at least one proteolytic enzyme. Various aspects of the invention can, however, include at least one step comprising co-drying the protein hydrolysate/enzyme admixture after the desired degree of hydrolysis has been achieved. The period of time during which the protein/enzyme admixture is held is from about 1 to about 72 hours, or subranges of that time period such as, for example, from about 4 to about 8 hours, from about 6 to about 8 hours, from about 6 to about 24 hours, from about 6 to about 72 hours, etc., the time being determined by one of skill in the art according to the degree of hydrolysis desired in the hydrolysate produced thereby. Methods for determining the degree of hydrolysis of one or more proteins are well-known to those of skill the art.

The invention also relates to a protein hydrolysate/enzyme composition, wherein the composition comprises a co-dried product of hydrolyzed protein and one or more enzyme(s) used to hydrolyze the protein, according to the method. Such a composition may be used as a dietary supplement in and of itself, and may, in various aspects, be combined with other ingredients such as, for example, flavorings, vitamins, antioxidant compositions, colorings, non-protease enzymes in addition to the proteases, or other ingredients and/or excipients which are commonly used in the supplement industry. Compositions of the invention may also be ideal for use in the sports/performance nutrition industry, in which both protein hydrolysates and enzyme supplements constitute a significant product growth area. Compositions of the invention may also be suitable, for example, for use by individuals who have problems with protein digestion, by elderly individuals who need to supplement their diets with readily-available protein sources, and others. The inventors have confirmed that even after the protein has been hydrolyzed, the enzyme in the co-dried hydrolysate/enzyme product retains significant proteolytic activity (see Table 4).

Conventional wisdom dictates that methods for the enzymatic hydrolysis of proteins include a heating step to achieve an optimal temperature range for the enzyme(s) used to hydrolyze the protein, and often include a second heating step to raise the temperature sufficiently to deactivate the enzyme(s). The method disclosed herein by the inventors would therefore, according to conventional wisdom, be considered to be utilizing the enzyme(s) at "sub-optimal" temperatures because, in various aspects, the method is performed within a temperature range of from about 33 to about 50 degrees Fahrenheit (which includes subranges within that range, such as 33 to 45 degrees Fahrenheit, 45 to 50 degrees, for example). Refrigeration temperatures for food, for example, generally fall within the range of from about 33 to about 45 degrees F.

As mentioned previously, the inventors have discovered that with this more simplified method they can produce high-quality protein hydrolysates with the desired degree of hydrolysis, while decreasing the costs associated with the production of protein hydrolysates by conventional methods and maintaining enzyme activity in a protein/enzyme composition produced by the method. These costs include, for example, reduced energy costs, due to the lack of one or more heating step(s), reduced costs of chemicals such as those used for pH adjustment, because they are not required in the present method, and reduced equipment costs and facilities costs, since the method requires fewer containment vessels and processing space than do certain multi-step hydrolysis methods. For example, addition of chemicals for pH adjustment generally creates changes in the mineral composition of a product that has been pH-adjusted, and these differences in mineral composition can create the need for further processing which is not necessary for the method of the invention. Such types of chemical addition can be, but are not limited to, the use of sodium hydroxide, which will increase the sodium and ash content, hydrochloric acid, which will increase the chloride and ash content, and phosphoric acid, which will increase the phosphorous and ash content.

In various aspects, the protein is whey protein, which can be selected from the group consisting of whey protein isolate, whey protein concentrate, and combinations thereof. Enzymes may be selected from the group consisting of plant animal, fungal, bacterial, and algal origins, as well as combinations thereof. For example, a variety of enzyme mixes for use in the food industry are commercially available from DSM (Heerlen, Netherlands), including Maxipro® UPG, Maxipro® CPP and Accelerzyme® CPG. Specialty Enzymes & Biotechnologies Co. (Chino, Calif.) also produces enzymes and enzyme mixes for use in the protein hydrolysis in the food industry. Identification of enzymes for use in the method is well within the expertise of those of skill in the art. It should be understood by those of skill in the art that not all hydrolysates have the same degree of hydrolysis, and that different degrees of hydrolysis may be desirable for different purposes for which the hydrolysate is intended. Therefore, the term "the desired degree of hydrolysis" means the level of hydrolysis that one of skill in the art has intended for the particular purpose for which the product is made, and "hydrolysate" means protein that has been hydrolyzed to that desired degree of hydrolysis, which can vary according to the intentions of the formulator for use of the hydrolysate. For many commonly used proteolytic enzymes, the inventors have determined that a significant degree of hydrolysis occurs within the first 1 to 4 hours after the enzyme/protein admixture is created, as shown in FIG. 1. Those of skill in the art will also be aware that extensive holding of the enzyme/protein admixture (e.g., well beyond 72 hours) may increase the tendency for gelation of at least a portion of the protein to occur, and may increase the opportunity for bacterial growth in the product before drying.

Some aspects of the invention may be described as a method comprising the step of performing protein hydrolysis by admixing at least one protein and at least one proteolytic enzyme under refrigeration temperatures to produce a protein hydrolysate/enzyme admixture and co-drying the protein hydrolysate/enzyme admixture, the method being performed without an enzyme activation step comprising the addition of heat, without an enzyme deactivation step, and without a step of pH adjustment.

As used herein, the singular forms "a," "and" and "the" include plural references unless the context clearly dictates otherwise. The invention is described herein as "comprising" certain elements, limitations, etc., and it will be understood by those of skill in the art that it is also within the scope of the invention to be more narrowly described as "consisting of" or "consisting essentially" of disclosed elements, limitations, etc., as well. "Whey protein," such as "whey protein concentrate," "whey protein isolate," and/or combinations thereof, will be used in the description of the invention. However, it will be understood by those of skill in the art that this method may also be used for the hydrolysis of other proteins, including, for example, those of animal and/or plant origin, such as soy protein(s). "Holding" is a term used in the industry to denote allowing a composition to sit, incubate, etc. to allow time for a desired process or reaction to occur. "Agitation," as used herein, may be intermittent or continuous.

In the method of the invention, whey protein (e.g., whey protein concentrate, whey protein isolate, or combinations thereof) is added to a suitable holding tank. Generally, a suitable holding tank will be, for example, a stainless steel tank which is Grade A certified. Whey protein concentrate is often, for example, held within silos, while whey protein isolate is often held within storage tanks. Enzyme is added at a concentration that is based on the solids content of the whey protein product that has been added to the tank. The whey protein and enzyme admixture is then held in the tank, with agitation, for a period of from about 1 to about 72 hours to produce a hydrolyzed protein product. By way of example, the enzyme/protein admixture may be held for a period of from about 4 to about 8 hours, from about 6 to about 8 hours, from about 6 to about 24 hours, from about 6 to about 72 hours, etc. As indicated in FIG. 1, the most significant amount of hydrolysis may occur within the first one to eight hours. In various aspects of the invention, the temperature at which the admixture is held is from about 33 to about 45 degrees Fahrenheit.

Agitation may be produced by various means, such as, for example agitators/mixers manufactured by Walker Engineered Products, New Lisbon, Wis. USA. Silos, for example, are available with machinery to produce either horizontal or vertical agitation. Holding the admixture for a period of time, especially when mild agitation is employed, produces a hydrolyzed protein product. The hydrolyzed protein product is then dried. For example, one common and very efficient method for drying the hydrolyzed protein product is spray-drying. The final spray-dried product can then be packaged and shipped for use as an ingredient in foods, beverages, supplements, and/or other products for which hydrolyzed protein, and especially hydrolyzed whey protein, is a desired ingredient. One significant advantage of the present method is that the enzyme is not subjected to a heat or chemical deactivation step. Therefore, the spray-dried hydrolysate has residual enzyme activity, which may be especially desirable for certain products, such as those used in the performance nutrition industry, into which the hydrolysate may be incorporated.

Conventional methods generally involve dilution of protein as an early step in the method for producing hydrolysates. Without being bound by theory, the inventors believe, however, that increasing the concentration of the solids in the initial protein product to be hydrolyzed optimizes the opportunity for interaction between the enzyme(s) and the protein(s). For example, the inventors used a product with a syrupy consistency, having a 33% solids content, with excellent results. Generally, it can be desirable to start with at least about 30 percent solids (w/v) in the initial protein product that is to be subjected to hydrolysis. Higher solids content can also aid in spray-drying the final product. Perhaps even more importantly, however, performing the method without diluting the protein (i.e., at a higher solids content) can decrease water usage, leading to a potential reduction in overall costs of thousands, and perhaps tens of thousands of dollars annually, as well as increasing conservation of a valuable natural resource.

In the present method, enzyme may be added either as the tank starts to fill, during the fill process, or at the end of the fill process. Those of skill in the art will be aware that the amount of enzyme will depend upon the particular enzyme(s) used, amounts commonly being calculated by those of skill in the art according to the amount of protein and particular enzyme(s) used to provide the proteolytic activity. Although the types of enzymes commonly used for protein hydrolysis may generally be considered "out of their temperature range" without a heating step, heating is not a requirement in the present method, and the temperature during processing is generally at or below 50 degrees Fahrenheit (10 degrees Celsius). Conventional processes usually involve pH adjustment using, for example, potassium hydroxide (KOH) or sodium hydroxide (NaOH). For example, the method described in U.S. Pat. No. 8,101,377 (M. V. Blanton et al., 24 Jan. 2012) requires pH adjustment, but the inventors have discovered that pH adjustment is not necessary and, in fact, as explained earlier, can result in the need for added steps in addition to the step of pH adjustment. In the method of the invention, the pH will naturally start at about 6.4, and will generally decrease during the hydrolysis process to below pH 6.0. The pH may drop within the range of about 5.0 to about 6.0.

The invention may also be described further by means of the following non-limiting examples.

Examples

Preparation of Hydrolysate from Whey Protein Isolate

Two kilograms of whey protein isolate (30% w/v) was added to a stainless steel holding tank, with the addition of DPP74 enzyme (dipeptidyl peptidase blend, DSM, Netherlands) at amounts shown in Table 1. The temperature of the admixture was about 43 degrees Fahrenheit. The admixture was held, with gentle agitation (BDC1850 stirrer, Caframo Ltd., Ontario, Canada) for a period of 48 hours. Drying was done using a spray-dryer (GEO Niro A/S, Soeborg, Denmark). Table 1 lists the degrees of hydrolysis achieved for each batch.

TABLE 1

Hydrolysate from Whey Protein Isolate

| Protein | Percent Enzyme | DH | Moisture | Carbohydrate | Protein | Ash | Fat | Time | Temp |
|---|---|---|---|---|---|---|---|---|---|
| WPI | .025% | 1.67 | 3.67 | 4.97 | 87.7 | 2.82 | 0.84 | 48 hours | 43° F. |
| WPI | .16% | 7.14 | 3.76 | 5.42 | 86.94 | 2.92 | 0.96 | 48 hours | 43° F. |
| WPI | .08% | 10.98 | 4.27 | 3.62 | 88.66 | 2.41 | 1.04 | 48 hours | 43° F. |
| WPI | .16% | 12.82 | 4.21 | 4.79 | 87.65 | 2.47 | 0.88 | 48 hours | 43° F. |

Degree of Hydrolysis vs Time—Whey Protein Isolate

Hydrolysis was performed as described above. Samples were taken at time points from 0 to 48 hours, and the degree of hydrolysis was measured for each sample. The experiment was run on two different days (A and B), using enzyme at 0.025% and 0.17% on each day. Results are shown in Table 2 and in FIG. 1.

TABLE 2

Degree of Hydrolysis vs Time - Whey Protein Isolate

| Hours | 0.025% A | 0.17% A | 0.025% B | 0.17% B |
|---|---|---|---|---|
| 0 | 0 | 0 | 0 | 0 |
| 2 | 1.60 | 6.93 | 2.72 | 7.89 |
| 4 | 1.48 | 7.68 | 2.37 | 10.63 |
| 9 | 1.18 | 8.01 | 1.96 | 10.43 |
| 24 | 1.82 | 8.58 | 2.51 | 10.97 |
| 48 | 1.74 | 9.54 | 2.80 | 11.51 |

Preparation of Hydrolysate from Whey Protein Concentrate

Two kilograms of whey protein concentrate (26%) was added to a stainless steel holding tank, with the addition of DPP74 enzyme (dipeptidyl peptidase blend, DSM, Netherlands) at amounts shown in Table 3. The temperature of the admixture was about 43 degrees Fahrenheit. The admixture was held, with gentle agitation (BDC1850 stirrer, Caframo Limited, Georgian Bluffs, Ontario, Canada) for a period of 48 hours. Table 3 lists the degrees of hydrolysis achieved for each batch.

TABLE 3

Hydrolysate from Whey Protein Concentrate

| Protein | Percent Enzyme | DH | Moisture | Carbohydrate | Protein | Ash | Fat | Time | Temp |
|---|---|---|---|---|---|---|---|---|---|
| WPC | .03% enzyme | 1.15 | 3.72 | 5.39 | 76.77 | 3.87 | 10.25 | 48 hours | 43° F. |
| WPC | .08% enzyme | 2.11 | 3.17 | 6.40 | 75.75 | 3.77 | 10.37 | 48 hours | 43° F. |
| WPC | .16% Enzyme | 5.27 | 3.45 | 6.62 | 75.72 | 3.83 | 10.38 | 48 hours | 43° F. |

Assessment of Enzyme Activity after Co-Drying Protein/Enzyme Admixture

Activity of enzymes after hydrolysis was performed according to the method and the resulting product was spray-dried (i.e., hydrolysate and enzymes were co-dried). Results are shown in Table 4.

TABLE 4

Protease Activity Post Hydrolysis & Spray-Drying

| Protein | Percent Enzyme | DH | Time (Hours) | Temp | Protease Activity |
|---|---|---|---|---|---|
| WPI | .08 | 10.98 | 48 | 43 F. | .0580 |
| WPI | .16 | 12.82 | 48 | 43 F. | .3540 |

What is claimed is:

1. A method for producing a hydrolyzed whey protein product, the method comprising:
   a) admixing at least one proteolytic enzyme with at least one whey protein to produce a protein/enzyme admixture, and
   b) holding the protein/enzyme admixture for a period of time from about 1 to about 72 hours under agitation to produce a protein hydrolysate/enzyme admixture, wherein the method does not comprise the step of adjusting the pH to optimize the activity of, or to deactivate, the at least one proteolytic enzyme.

2. The method of claim 1 further comprising the step of drying the protein hydrolysate/enzyme admixture.

3. The method of claim 2 wherein the step of drying the protein hydrolysate/enzyme admixture is performed by spray-drying.

4. The method of claim 1 wherein the whey protein comprises a solution of at least about 30 percent w/v.

5. The method of claim 1 wherein the period of time during which the protein/enzyme admixture is held comprises from about 4 to about 8 hours.

6. The method of claim 1 wherein the period of time during which the protein/enzyme admixture is held comprises from about 6 to about 8 hours.

7. The method of claim 1 wherein the period of time during which the protein/enzyme admixture is held comprises from about 6 to about 24 hours.

8. The method of claim 1 wherein the period of time during which the protein/enzyme admixture is held comprises from about 6 to about 72 hours.

9. The method of claim 1 wherein the protein/enzyme admixture is held at a temperature of from about 33 to about 50 degrees Fahrenheit.

10. The method of claim 1 wherein the at least one proteolytic enzyme is selected from the group consisting of proteolytic enzymes of plant, animal, fungal, algal, and bacterial origin, and combinations thereof.

11. The method of claim 1, wherein step (a) is performed without heating the protein, at least one proteolytic enzyme, protein/enzyme admixture, or a combination thereof, to increase the activity of the enzyme in the protein/enzyme admixture.

12. The method of claim 1, wherein the protein hydrolysate/enzyme admixture is not heated to deactivate the enzyme during step (b).

* * * * *